(12) United States Patent
Zhang et al.

(10) Patent No.: US 10,534,207 B2
(45) Date of Patent: Jan. 14, 2020

(54) FIXTURE FOR DISPLAY MODULE INSPECTION

(71) Applicants: BOE Technology Group Co., Ltd., Beijing (CN); BOE (Hebei) Mobile Display Technology Co., Ltd., Hebei (CN)

(72) Inventors: Ping Zhang, Beijing (CN); Zhen Wu, Beijing (CN)

(73) Assignees: BOE TECHNOLOGY GROUP CO., LTD., Beijing (CN); BOE (HEBEI) MOBILE DISPLAY TECHNOLOGY CO., LTD., Beijing (CN)

( * ) Notice: Subject to any disclaimer, the term of this patent is extended or adjusted under 35 U.S.C. 154(b) by 121 days.

(21) Appl. No.: 15/647,596

(22) Filed: Jul. 12, 2017

(65) Prior Publication Data

US 2018/0059468 A1 Mar. 1, 2018

(30) Foreign Application Priority Data

Aug. 30, 2016 (CN) .......................... 2016 1 0767972

(51) Int. Cl.
| | | |
|---|---|---|
| *G02F 1/13* | (2006.01) | |
| *G01N 21/01* | (2006.01) | |
| *G09G 3/00* | (2006.01) | |
| *F16M 11/04* | (2006.01) | |
| *H01L 21/66* | (2006.01) | |
| *G02F 1/1362* | (2006.01) | |

(Continued)

(52) U.S. Cl.
CPC ........... *G02F 1/1309* (2013.01); *F16M 11/04* (2013.01); *G01N 21/01* (2013.01); *G09G 3/006* (2013.01); *H01L 22/30* (2013.01); *F16M 2200/00* (2013.01); *G01N 2021/9513* (2013.01); *G02F 1/133308* (2013.01); *G02F 2001/136254* (2013.01); *G02F 2203/69* (2013.01); *G06T 2207/30121* (2013.01)

(58) Field of Classification Search
CPC ....... G02F 1/1309; G02F 2001/136254; G02F 2203/69; G09G 3/006; G01N 21/01; G01N 2021/0106; G01N 2021/9513; G01N 21/8803; G06T 2207/30121; H01L 22/30

See application file for complete search history.

(56) References Cited

U.S. PATENT DOCUMENTS

| | | | | |
|---|---|---|---|---|
| 8,794,579 B2 * | 8/2014 | Sturman | .............. | F16M 11/105 248/284.1 |
| 2015/0305518 A1 * | 10/2015 | Galant | ................. | F16M 11/041 248/551 |

* cited by examiner

*Primary Examiner* — Paisley L Wilson
(74) *Attorney, Agent, or Firm* — Westman, Champlin & Koehler, P.A.

(57) ABSTRACT

A fixture for display module inspection is disclosed. The fixture includes a base, a lower rotatable body pivotally mounted on the base, a middle rotatable body hinged with the lower rotatable body, an upper rotatable body hinged with the middle rotatable body and a carrier fixedly connected to the upper rotatable body for carrying a display module. A rotation axis of the lower rotatable body and a rotation axis of the middle rotatable body are arranged orthogonally to each other, the rotation axis of the middle rotatable body and a rotation axis of the upper rotatable body are arranged orthogonally to each other. Rotation position locking mechanisms are respectively provided between the lower rotatable body and the base, between the middle rotatable body and the lower rotatable body, and between the upper rotatable body and the middle rotatable body.

15 Claims, 3 Drawing Sheets

(51) Int. Cl.
*G01N 21/95* (2006.01)
*G02F 1/1333* (2006.01)

FIXTURE FOR DISPLAY MODULE INSPECTION

CROSS-REFERENCE TO RELATED APPLICATION

This application claims the benefit of Chinese Patent Application No. 201610767972.2 filed on Aug. 30, 2016 in the State Intellectual Property Office of China, the disclosure of which is incorporated in entirety herein by reference.

BACKGROUND

Technical Field

Embodiments of the present disclosure relate to a field of display technology, and more particularly, to a fixture for display module inspection.

Description of the Related Art

In a flat panel display device, Thin Film Transistor Liquid Crystal Display (TFT-LCD) has some characteristics, such as small volume, low power consumption, relatively low manufacturing cost and no radiation, therefore it occupies a leading position in a current flat panel display market.

In the production process of TFT-LCD, it is necessary for an inspector to implement a screen inspection on a liquid crystal module, which has been powered up, by his naked eyes. A surrounding area of the screen of the liquid crystal module has a high incidence of badness, thus it is necessary for the inspector to swing his head several times during the inspection so as to observe and inspect the screen by different viewing angles.

The above-mentioned prior art has drawbacks in that, it is hard to control the viewing angle when the inspector inspects the screen of the powered liquid crystal module and it often causes a missing inspection or an excessive inspection, thereby resulting in a low inspection accuracy and adversely affecting factory quality of the product. In addition, the inspector needs to frequently swing his head to change the viewing angle, as a result, it not only has a low inspection efficiency, but also tends to cause fatigue for the inspector.

SUMMARY

In order to at least partially overcome the drawbacks of the prior art, embodiments of the present disclosure provide a fixture for display module inspection to improve accuracy of inspection on a screen of a powered display module, improve inspection efficiency and reduce labor intensity of the inspector.

According to an embodiment of the present disclosure, there is provided a fixture for display module inspection, comprising a base, a lower rotatable body pivotally mounted on the base, a middle rotatable body hinged with the lower rotatable body, an upper rotatable body hinged with the middle rotatable body and a carrier fixedly connected to the upper rotatable body for carrying a display module, wherein a rotation axis of the lower rotatable body and a rotation axis of the middle rotatable body are arranged orthogonally to each other, the rotation axis of the middle rotatable body and a rotation axis of the upper rotatable body are arranged orthogonally to each other, and wherein rotation position locking mechanisms are respectively provided between the lower rotatable body and the base, between the middle rotatable body and the lower rotatable body, and between the upper rotatable body and the middle rotatable body.

Optionally, the rotation position locking mechanism comprises a plurality of limit pits arranged in an annular shape and a plunger assembly facing towards an annular arrangement region of the plurality of limit pits, the plunger assembly being configured to be successively limited in each of the limit pits.

Optionally, the rotation position locking mechanism further comprises an annular guiding groove in which the plurality of limit pits are located.

Optionally, the plurality of limit pits are uniformly distributed.

Optionally, the number of the plunger assemblies is not less than two.

Optionally, the plunger assembly comprises a top bead, a threaded mounting portion, and a spring connecting the top bead with the threaded mounting portion, the top bead facing towards the annular arrangement region of the plurality of limit pits.

Optionally, the limit pits of the rotation position locking mechanism between the lower rotatable body and the base are arranged in the base, and the plunger assembly of the rotation position locking mechanism between the lower rotatable body and the base is arranged in the lower rotatable body, wherein the limit pits of the rotation position locking mechanism between the middle rotatable body and the lower rotatable body are arranged in the middle rotatable body, and the plunger assembly of the rotation position locking mechanism between the middle rotatable body and the lower rotatable body is arranged in the lower rotatable body, and wherein the limit pits of the rotation position locking mechanism between the upper rotatable body and the middle rotatable body are arranged in the upper rotatable body, and the plunger assembly of the rotation position locking mechanism between the upper rotatable body and the middle rotatable body is arranged in the middle rotatable body.

Optionally, the base comprises a base body and a bearing seat provided on the base body, and the lower rotatable body is pivotally mounted in the bearing seat by a bearing.

Optionally, the fixture further comprises a carrier supporting plate fixedly connected to the upper rotatable body, wherein the carrier is detachably connected to the carrier supporting plate.

Optionally, the carrier is connected to the carrier supporting plate in a magnetic attraction manner and the carrier and the carrier supporting plate are positioned by a plurality of locating pins.

DETAILED DESCRIPTION OF PREFERRED EMBODIMENTS

In order to improve accuracy of inspection on a screen of a powered display module, improve inspection efficiency and reduce labor intensity of an inspector, there is provided a fixture for display module inspection in an embodiment of the present disclosure. In order to clearly set forth objectives, technical solutions and advantages of the present disclosure, the present disclosure will be described in further detail with reference to the following embodiments now.

Figure 1:
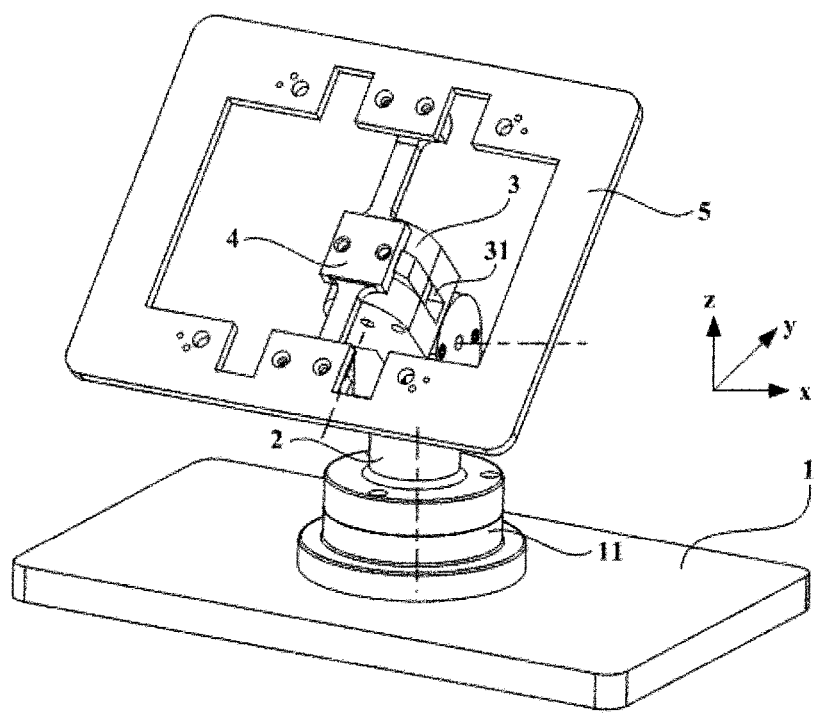
FIG. 1 is a schematic view of a fixture for display module inspection according to an embodiment of the present disclosure.
Figure 2:
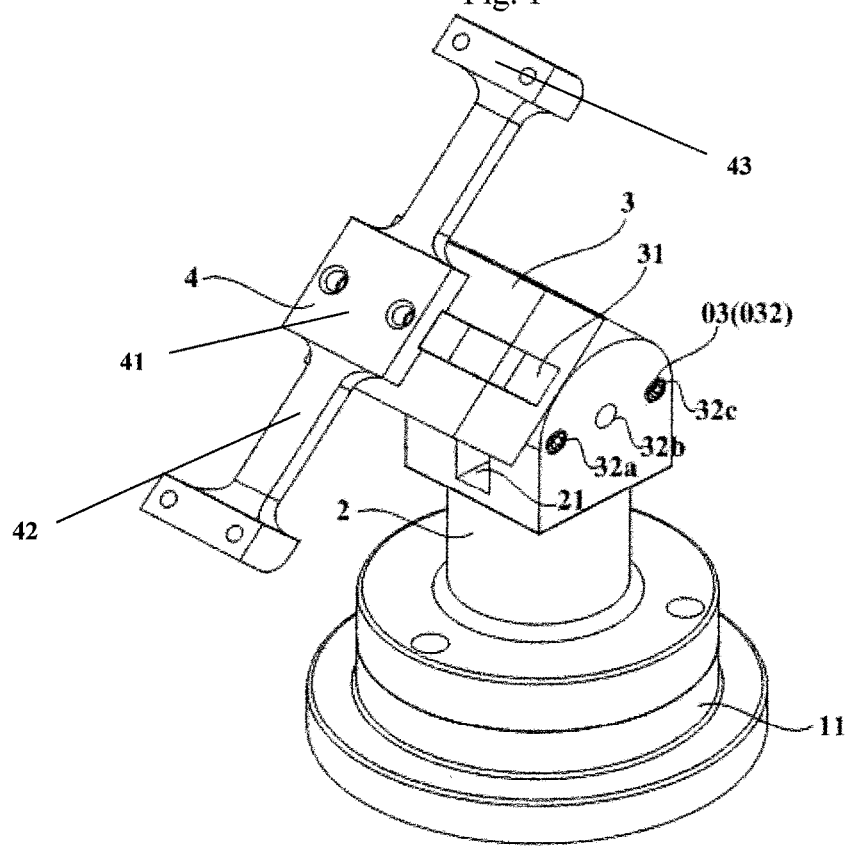
FIG. 2 is a schematic view showing connection relationship of a lower rotatable body, a middle rotatable body and an upper rotatable body of a fixture for display module inspection according to an embodiment of the present disclosure.

As shown in FIGS. 1 and 2, the fixture for display module inspection according to the embodiment of the present disclosure includes a base 1, a lower rotatable body 2 pivotally mounted on the base 1, a middle rotatable body 3 hinged with the lower rotatable body 2, an upper rotatable body 4 hinged with the middle rotatable body 3 and a carrier fixedly connected to the upper rotatable body 4 for carrying a display module (the carrier may be directly fixed to the upper rotatable body 4, or alternatively, it may be arranged on a carrier supporting plate 5 fixed to the upper rotatable body 4, the latter structure is adopted in this embodiment). A rotation axis of the lower rotatable body 2 and a rotation axis of the middle rotatable body 3 are arranged orthogonally to each other, the rotation axis of the middle rotatable body 3 and a rotation axis of the upper rotatable body 4 are arranged orthogonally to each other. Rotation position locking mechanisms are respectively provided between the lower rotatable body 2 and the base 1, between the middle rotatable body 3 and the lower rotatable body 2, and between the upper rotatable body 4 and the middle rotatable body 3.

In the embodiment of the present disclosure, the rotation axis of the lower rotatable body 2 is vertically arranged in z-direction, the rotation axis of the middle rotatable body 3 is horizontally arranged in x-direction, and the rotation axis of the upper rotatable body 4 moves with the rotation of the middle rotatable body 3 in terms of position, but a projection of the rotation axis of the upper rotatable body 4 on a horizontal plane is always arranged in y-direction.

In the present disclosure, detailed structures of the lower rotatable body 2, the middle rotatable body 3 and the upper rotatable body 4 are not limited to these types. For example, in the embodiment shown in FIGS. 1 and 2, a first opening groove 21 is provided in an upper portion of the lower rotatable body 2, a lower portion of the middle rotatable body 3 extends into the first opening groove 21 and is hinged with the upper portion of the lower rotatable body 2 by means of a pin (provided at a mounting hole 32b), and the middle rotatable body 3 can be rotated around a rotation axis in the first opening groove 21. A second opening groove 31 is provided in an upper portion of the middle rotatable body 3, a projection of the second opening groove 31 and a projection of the first opening groove 21 on the horizontal plane are arranged orthogonally to each other, and a lower portion of the upper rotatable body 4 extends into the second opening groove 31 and is hinged with the upper portion of the middle rotatable body 3 by means of a pin.

When the fixture according to the embodiment of the present disclosure is used to inspect the screen of powered display module, an inspector can adjust relative rotation positions between the lower rotatable body 2 and the base 1, between the middle rotatable body 3 and the lower rotatable body 2, between the upper rotatable body 4 and the middle rotatable body 3, thus it can achieve a free rotation of the display module, without needing to frequently swing his head. The relative rotation positions between the lower rotatable body 2 and the base 1, between the middle rotatable body 3 and the lower rotatable body 2, between the upper rotatable body 4 and the middle rotatable body 3 may be locked by the respective rotation position locking mechanisms, so that the inspector can observe and inspect the display module by a specific viewing angle. Compared with the prior art, the use of the fixture improves the accuracy of the inspection on the screen of the powered display module and the inspection efficiency, and reduces the labor intensity of the inspector.

Detailed structures of the rotation position locking mechanism are not limited in the present disclosure, for example, a rubber gasket which has a relatively large frictional resistance may be provided.

Figure 3:
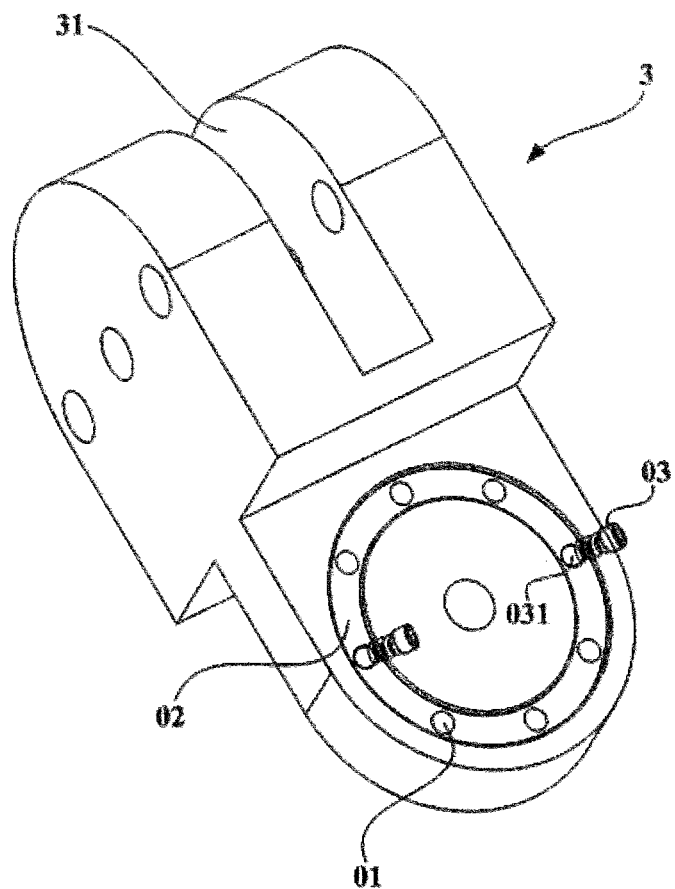
FIG. 3 is a schematic view of a middle rotatable body and a plunger assembly of a fixture for display module inspection according to an embodiment of the present disclosure.
Figure 4:
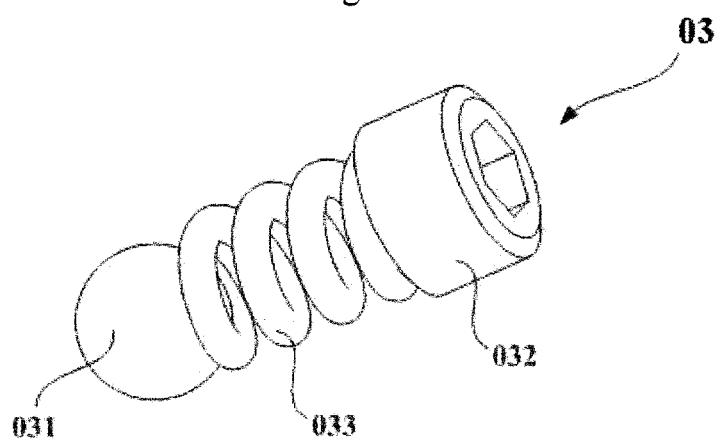
FIG. 4 is a schematic view of a plunger assembly of a fixture for display module inspection according to an embodiment of the present disclosure.

As shown in FIGS. 2 and 3, in an optional embodiment of the present disclosure, the rotation position locking mechanism comprises a plurality of limit pits 01 arranged in an annular shape and a plunger assembly 03 facing towards an annular arrangement region of the plurality of limit pits 01, a top bead 031 of the plunger assembly 03 may be successively housed or limited in each of the limit pits 01. As shown in FIGS. 3 and 4, the structure of the plunger assembly 03 comprises a top bead 031, a threaded mounting portion 032, and a spring 033 connecting the top bead 031 with the threaded mounting portion 032, the top bead 031 faces towards the annular arrangement region of the above-described plurality of limit pits 01.

When two members which are respectively provided with the above-described plurality of limit pits 01 and the plunger assembly 03 are rotated relative to each other, the top bead 031 of the plunger assembly may be successively limited in each of the limit pits 01. The two members refer to the base 1 and the lower rotatable body 2, the middle rotatable body 3 and the lower rotatable body 2, or the upper rotatable body 4 and the middle rotatable body 3 herein. When the top bead 031 is located in one limit pit 01 and an external force for rotating the two members relative to each other is cancelled, the relative rotation position of the two members is locked.

Please refer to FIG. 1, in this embodiment, the limit pits of the rotation position locking mechanism between the lower rotatable body 2 and the base 1 are arranged in the base 1, the plunger assembly of the rotation position locking mechanism between the lower rotatable body 2 and the base 1 is arranged in the lower rotatable body 2, and the threaded mounting portion of the plunger assembly is screwed to the lower rotatable body 2; the limit pits of the rotation position locking mechanism between the middle rotatable body 3 and the lower rotatable body 2 are arranged in the middle rotatable body 3, the plunger assembly of the rotation position locking mechanism between the middle rotatable body 3 and the lower rotatable body 2 is arranged in the lower rotatable body 2, and the threaded mounting portion of the plunger assembly is screwed to the lower rotatable body 2; the limit pits of the rotation position locking mechanism between the upper rotatable body 4 and the middle rotatable body 3 are arranged in the upper rotatable body 4, the plunger assembly of the rotation position locking mechanism between the upper rotatable body 4 and the middle rotatable body 3 is arranged in the middle rotatable body 3, and the threaded mounting portion of the plunger assembly is screwed to the middle rotatable body 3. As shown in FIG. 2, the upper portion of the lower rotatable body 2 has three mounting holes 32a, 32b, 32c, wherein the mounting hole 32a and the mounting hole 32c are threaded through holes for receiving the plunger assembly 03, and the mounting hole 32b is a through hole located in the middle of the mounting hole 32a and the mounting hole 32c for receiving a hinge shaft of the lower rotatable body 2 and the middle rotatable body 3. The mounting holes in the middle rotatable body 3 are arranged in a similar manner to the mounting holes in the lower rotatable body 2.

The limit pits 01 and the plunger assembly 03 need to be respectively arranged on two opposite rotation surfaces of the two members which are rotated relative to each other, and the structures shown in FIGS. 1 to 3 are one exemplary example of the present disclosure. It should be understood that, in other embodiments of the present disclosure, the limit pits of the rotation position locking mechanism between the lower rotatable body and the base may also be arranged in the lower rotatable body, and the plunger assembly of the rotation position locking mechanism between the lower rotatable body and the base may be arranged in the base; the limit pits of the rotation position locking mechanism between the middle rotatable body and the lower rotatable body may be arranged in the lower rotatable body, and the plunger assembly of the rotation position locking mechanism between the middle rotatable body and the lower rotatable body may be arranged in the middle rotatable body; the limit pits of the rotation position locking mechanism between the upper rotatable body and the middle rotatable body may be arranged in the middle rotatable body, and the plunger assembly of the rotation position locking mechanism between the upper rotatable body and the middle rotatable body may be arranged in the upper rotatable body.

Please refer to FIG. 3 again, the rotation position locking mechanism further comprises an annular guiding groove 02 in which the plurality of limit pits 01 are located. The annular guiding groove 02 can guide the movement of the top bead 031 of the plunger assembly 03 when the lower rotatable body 2 rotates relative to the base 1, or the middle rotatable body 3 rotates relative to the lower rotatable body 2, or the upper rotatable body 4 rotates relative to the middle rotatable body 3, thus it can improve the stability of the rotation and the fitting between the members may be easily achieved.

In an optional embodiment of the present disclosure, the plurality of limit pits are uniformly distributed. For example, in an embodiment, the number of limit pits is eight and they are uniformly distributed. In this way, if one of the two members capable of rotating relative to each other is rotated by 45 degrees, then they may be locked in a rotation position. In addition, optionally, the number of the plunger assemblies is not less than two. With this design, they may be locked in at least two relative rotation positions, thereby further improving the reliability of the structure.

Taking the rotation of the middle rotatable body 3 relative to the lower rotatable body 2 in the embodiment shown in FIGS. 1 to 3 as an example, when the top bead 031 of the plunger assembly 03 is limited in one of the limit pits 01, the rotation position of the middle rotatable body 3 relative to the lower rotatable body 2 is locked. In case of no external force, the middle rotatable body 3 cannot rotate relative to the lower rotatable body 2. When the middle rotatable body 3 is forced to rotate relative to the lower rotatable body 2, the top bead 031 of the plunger assembly 03 slides out of the limit pit 01 and slides in the annular guiding groove 02, and the spring is compressed. If the top bead 031 slides into the next limit pit and the external force is removed, then the rotation position will be locked again.

In an optional embodiment of the present disclosure, as shown in FIG. 1, since the lower rotatable body 2 is heavy loaded, the base 1 comprises a base body and a bearing seat 11 provided on the base body, and the lower rotatable body 2 is pivotally mounted in the bearing seat 11 by a bearing. With this embodiment, it can reduce the friction between the lower rotatable body 2 and the base 1, and improve the rotation accuracy, thereby improving the stability and reliability of the structure.

Figure 5:
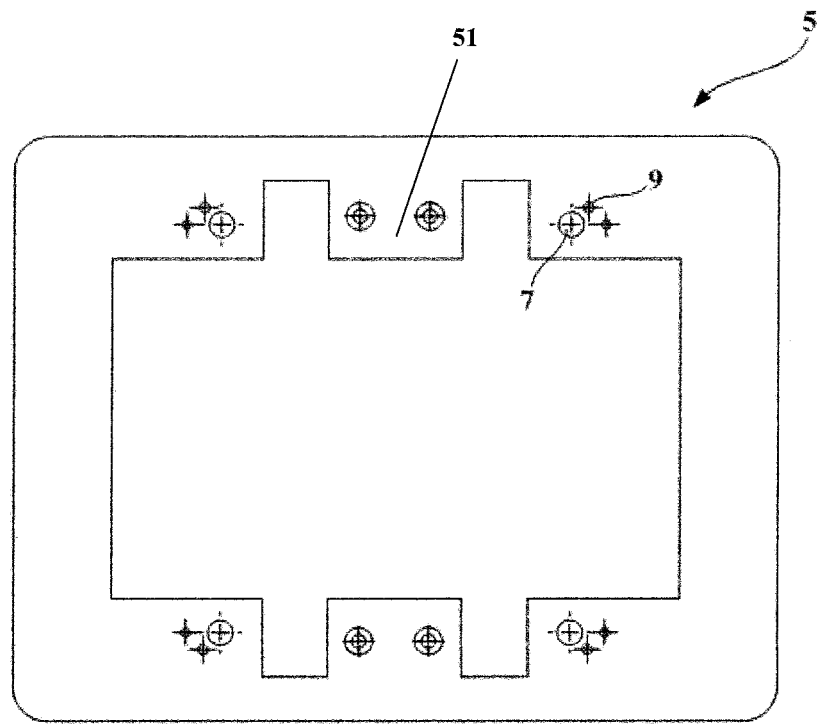
FIG. 5 is a schematic view of a carrier supporting plate of a fixture for display module inspection according to an embodiment of the present disclosure.
Figure 6:
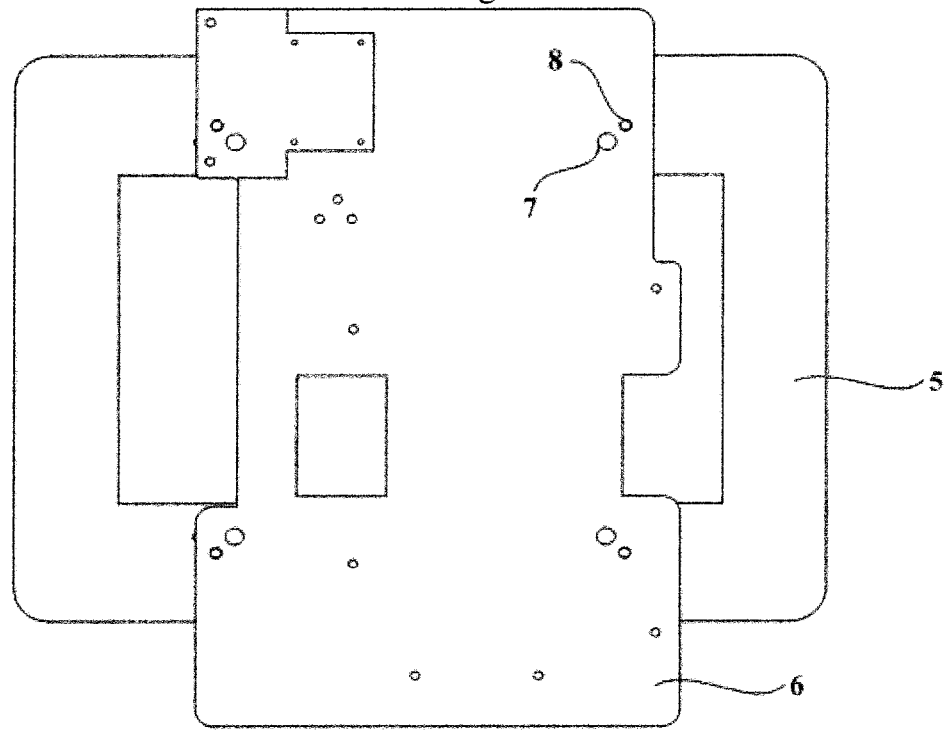
FIG. 6 is a schematic view showing connection relationship of a carrier and a carrier supporting plate of a fixture for display module inspection according to an embodiment of the present disclosure.

As shown in FIGS. 1, 5 and 6, in this embodiment, the fixture further comprises a carrier supporting plate 5 fixedly connected to the upper rotatable body 4, and the carrier 6 is detachably connected to the carrier supporting plate 5. If the model of the display module is changed, a carrier 6 matching with it can be replaced without needing to replace the entire fixture. Therefore, with this design, it can save the cost of the fixture and save the replacement time for the fixture. In other embodiments of the present disclosure, the carrier 6 may also be designed to be directly fixed to the upper rotatable body 4.

The upper rotatable body 4 may comprise an upper portion and a lower portion. As described above, the lower portion of the upper rotatable body 4 extends into the second opening groove 31 and is hinged with the upper portion of the middle rotatable body 3 by means of a pin. The upper portion of the upper rotatable body 4 comprises an intermediate platform 41, two extension arms 42 extending outwardly from the intermediate platform 41 and supporting portions 43 provided at ends of the respective extension arms 42 away from the intermediate platform 41. The carrier supporting plate 5 has a structure of square frame, with an opening in the center, and two protrusions 51 project from opposite edges of the square frame, respectively, wherein the supporting portion 43 and the protrusion 51 may be fixed to each other by for example screws. Further, a connection structure, such as a screw hole, is provided in the intermediate platform 41. With this connection structure, a matching connection structure in the display module may be connected to the connection structure in the intermediate platform 41, so that the display module is directly fixed to the upper rotatable body 4. In this case, the carrier supporting plate 5 and the carrier 6 may be omitted.

The specific detachable connection of the carrier 6 and the carrier supporting plate 5 is not limited in the present disclosure, for example, they may be connected by bolts. As shown in FIGS. 5 and 6, in an optional embodiment of the present disclosure, the carrier 6 is connected to the carrier supporting plate 5 in a magnetic attraction manner and the carrier 6 and the carrier supporting plate 5 are positioned by a plurality of locating pins 8. The carrier 6 and the carrier supporting plate 5 are respectively fitted with four magnets 7 at opposite positions, and the carrier 6 and the carrier supporting plate 5 are respectively provided with four pin holes 9 at opposite positions. After the carrier 6 is connected to the carrier supporting plate 5 in a magnetic attraction manner, four locating pins 8 are respectively inserted into the four pin holes 9, then the detachable connection of the carrier 6 and the carrier supporting plate 5 may be completed. The operation becomes very simple.

In the above-described embodiments of the present disclosure, the specific material used for each member of the fixture is not limited. Optionally, the base 1, the lower rotatable body 2, the middle rotatable body 3 and the upper rotatable body 4 are made of stainless steel or aluminum alloy materials, so as to ensure stability for the entire mechanism, and the carrier 6 and the carrier supporting plate 5 are made of bakelite materials having a good insulating property.

As shown in FIG. 1, after the display module is fixed to the carrier, the inspector applies a force to rotate the carrier supporting plate 5 around the rotation axis of the lower rotatable body 2, and then the lower rotatable body 2 may be locked in a specific rotation position. The inspector applies a force to rotate the carrier supporting plate 5 around the rotation axis of the middle rotatable body 3, and then the middle rotatable body 3 may be locked in a specific rotation position. The inspector applies a force to rotate the carrier supporting plate 5 around the rotation axis of the upper rotatable body 4, and then the upper rotatable body 4 may be locked in a specific rotation position. With the above adjustment operations, the display module is locked at a specific viewing angle, and the inspector can observe and inspect the display module at this specific viewing angle.

It will be apparent to those skilled in the art that various changes and modifications can be made to the embodiments of the present disclosure without departing from the spirit and scope of the present disclosure. Thus, the present disclosure is intended to incorporate such changes and modifications if these changes and modifications of the present disclosure fall within the scope of the claims of the present disclosure and the equivalents thereof.

What is claimed is:

1. A fixture for display module inspection, comprising a base, a lower rotatable body pivotally mounted on the base, a middle rotatable body hinged with the lower rotatable body, an upper rotatable body hinged with the middle rotatable body and a carrier fixedly connected to the upper rotatable body for carrying a display module,
    wherein a rotation axis of the lower rotatable body and a rotation axis of the middle rotatable body are arranged orthogonally to each other, the rotation axis of the middle rotatable body and a rotation axis of the upper rotatable body are arranged orthogonally to each other,
    wherein rotation position locking mechanisms are respectively provided between the lower rotatable body and the base, between the middle rotatable body and the lower rotatable body, and between the upper rotatable body and the middle rotatable body,
    wherein the rotation position locking mechanisms each comprise a plurality of limit pits arranged in an annular shape and at least one plunger assembly facing towards an annular arrangement region of the plurality of limit pits, one of the at least one plunger assembly being configured to be successively limited in each of the limit pits,
    wherein the limit pits of one of the rotation position locking mechanisms between the lower rotatable body and the base are arranged in the base, and the at least one plunger assembly of one of the rotation position locking mechanisms between the lower rotatable body and the base is arranged in the lower rotatable body,
    wherein the limit pits of one of the rotation position locking mechanisms between the middle rotatable body and the lower rotatable body are arranged in the middle rotatable body, and the at least one plunger assembly of one of the rotation position locking mechanisms between the middle rotatable body and the lower rotatable body is arranged in the lower rotatable body, and
    wherein the limit pits of one of the rotation position locking mechanisms between the upper rotatable body and the middle rotatable body are arranged in the upper rotatable body, and the at least one plunger assembly of one of the rotation position locking mechanisms between the upper rotatable body and the middle rotatable body is arranged in the middle rotatable body.

2. The fixture according to claim 1, wherein the rotation position locking mechanisms each further comprise an annular guiding groove in which the plurality of limit pits are located.

3. The fixture according to claim 2, further comprising a carrier supporting plate fixedly connected to the upper rotatable body, wherein the carrier is detachably connected to the carrier supporting plate.

4. The fixture according to claim 3, wherein the carrier is connected to the carrier supporting plate in a magnetic attraction manner and the carrier and the carrier supporting plate are positioned by a plurality of locating pins.

5. The fixture according to claim 1, wherein the plurality of limit pits are uniformly distributed.

6. The fixture according to claim 5, further comprising a carrier supporting plate fixedly connected to the upper rotatable body, wherein the carrier is detachably connected to the carrier supporting plate.

7. The fixture according to claim 6, wherein the carrier is connected to the carrier supporting plate in a magnetic attraction manner and the carrier and the carrier supporting plate are positioned by a plurality of locating pins.

8. The fixture according to claim 1, wherein there is more than one plunger assembly.

9. The fixture according to claim 8, further comprising a carrier supporting plate fixedly connected to the upper rotatable body, wherein the carrier is detachably connected to the carrier supporting plate.

10. The fixture according to claim 1, wherein the at least one plunger assembly comprises a top bead, a threaded mounting portion, and a spring connecting the top bead with the threaded mounting portion, the top bead facing towards the annular arrangement region of the plurality of limit pits.

11. The fixture according to claim 10, further comprising a carrier supporting plate fixedly connected to the upper rotatable body, wherein the carrier is detachably connected to the carrier supporting plate.

12. The fixture according to claim 1, wherein the base comprises a base body and a bearing seat provided on the base body, and the lower rotatable body is pivotally mounted in the bearing seat by a bearing.

13. The fixture according to claim 12, further comprising a carrier supporting plate fixedly connected to the upper rotatable body, wherein the carrier is detachably connected to the carrier supporting plate.

14. The fixture according to claim 1, further comprising a carrier supporting plate fixedly connected to the upper rotatable body, wherein the carrier is detachably connected to the carrier supporting plate.

15. The fixture according to claim 14, wherein the carrier is connected to the carrier supporting plate in a magnetic attraction manner and the carrier and the carrier supporting plate are positioned by a plurality of locating pins.

* * * * *